United States Patent
Curra et al.

(10) Patent No.: US 8,500,643 B2
(45) Date of Patent: Aug. 6, 2013

(54) MULTILAYER ULTRASOUND TRANSDUCER DEVICES FOR HIGH POWER TRANSMISSION AND WIDE-BAND RECEPTION AND ASSOCIATED SYSTEMS AND METHODS

(75) Inventors: Francesco P. Curra, Brier, WA (US); Peter J. Kaczkowski, Seattle, WA (US); Neil R. Owen, Bothell, WA (US)

(73) Assignee: University of Washington, Seattle, WA (US)

( * ) Notice: Subject to any disclaimer, the term of this patent is extended or adjusted under 35 U.S.C. 154(b) by 76 days.

(21) Appl. No.: 13/158,299

(22) Filed: Jun. 10, 2011

(65) Prior Publication Data
US 2012/0172721 A1    Jul. 5, 2012

Related U.S. Application Data

(60) Provisional application No. 61/353,582, filed on Jun. 10, 2010.

(51) Int. Cl.
*A61B 8/00* (2006.01)
*A61B 8/14* (2006.01)

(52) U.S. Cl.
USPC ............ 600/439; 600/438; 600/447; 600/459

(58) Field of Classification Search
USPC ........ 600/437, 439, 447, 459, 438; 29/25.35; 310/334
See application file for complete search history.

(56) References Cited

U.S. PATENT DOCUMENTS

| 5,744,898 A * | 4/1998 | Smith et al. ................... 310/334 |
| 7,344,501 B1 * | 3/2008 | Mohr et al. ................... 600/459 |
| 2012/0232388 A1 * | 9/2012 | Curra et al. ................... 600/438 |

OTHER PUBLICATIONS

Pernot, Mathieu et al. "Temperature Estimation Using Ultrasonic Spatial Compound Imaging". IEEE Transactions on Ultrasonics, ferroelectrics, and frequency control, vol. 51 No. 5, May 2004.*

* cited by examiner

*Primary Examiner* — Michael Rozanski
(74) *Attorney, Agent, or Firm* — Perkins Coie LLP

(57) ABSTRACT

Multilayer ultrasound transducer devices for high power transmission and wide-band reception and associated methods and systems are disclosed herein. An ultrasound transducer device in accordance with an embodiment of the present technology, for example, can include a first array of first transducers and a second array of second transducers that are oriented substantially parallel to one another. The first transducers can include a first piezoelectric material that is configured to transmit acoustic waves, and the second transducers can include a second piezoelectric material that is configured to receive echoes from the acoustic waves. The ultrasound transducer device can further include an electrical connection layer between the first and second arrays that is electrically coupled to the first and second transducers.

22 Claims, 7 Drawing Sheets

MULTILAYER ULTRASOUND TRANSDUCER DEVICES FOR HIGH POWER TRANSMISSION AND WIDE-BAND RECEPTION AND ASSOCIATED SYSTEMS AND METHODS

CROSS-REFERENCE TO RELATED APPLICATION(S)

This application claims the benefit of U.S. Provisional Application No. 61/353,582, entitled "MULTILAYER ULTRASOUND TRANSDUCER FOR HIGH POWER TRANSMISSION AND WIDE-BAND RECEPTION," filed Jun. 10, 2010, and incorporated herein by reference in its entirety.

STATEMENT REGARDING FEDERALLY SPONSORED RESEARCH OR DEVELOPMENT

This disclosure was made with government support under R01DK075090 awarded by National Institutes of Health (NIH). The government has certain rights in the invention.

TECHNICAL FIELD

The present technology relates generally to ultrasound imaging systems. In particular, several embodiments are directed toward multilayer ultrasound transducer devices for high power transmission and wide-band reception and associated systems and methods.

BACKGROUND

Ultrasound imaging systems can be used to visualize subcutaneous body structures, such as organs, muscles, embryos, joints, and vessels. Typically, ultrasound imaging systems include a processing station (e.g., a computer) operably coupled to an ultrasound scanner. The ultrasound scanner includes an array of piezoelectric transducers that are linked independently to the processing station by individual communication lines housed within a cable. During an ultrasound scan, each transducer in the array both transmits acoustic waves into a body toward a target site and detects echoes from the acoustic waves as they reflect off of internal body structures. The received echo data is then transmitted to the processing station, where images of the scanned internal structures can be formed, manipulated, and displayed.

Transmitting nonlinear acoustic waves can enhance the resolution of ultrasound imaging because harmonic frequencies have higher signal to noise and higher contrast to noise than the fundamental frequency. Additionally, the properties of the internal structures can impact the harmonic frequencies such that the harmonic scatter in the received echo may be used to derive information related to the internal structures. Conventional ultrasound scanners, however, lack the sensitivity to detect meaningful amounts of harmonic scatter.

DETAILED DESCRIPTION

The present technology is directed toward multilayer ultrasound transducer devices and associated systems and methods. In several embodiments, for example, an ultrasound transducer device can include two different piezoelectric transducers stacked atop of one another. The first transducer can launch acoustic waves into a medium (e.g., tissue) that become nonlinear through propagation, while the second transducer can have a wide bandwidth that detects the harmonic scatter in the echo of the acoustic wave as it is reflected from the medium. The harmonic scatter can be used to determine static and dynamic properties of the medium.

Certain specific details are set forth in the following description and in FIGS. 1-6 to provide a thorough understanding of various embodiments of the technology. For example, several embodiments of ultrasound transducer devices that propagate waves into human soft tissue are described in detail below. The present technology, however, may be used to image, characterize, and/or analyze other tissues and structures. Additionally, the terms "forward," "behind," and associated terms are used broadly throughout the disclosure to refer to the relative positioning of elements with respect to the general direction of the transmitted acoustic wave. For the purposes of this disclosure, "forward" means in the same general direction as the transmitted wave, and "behind" means in the opposite general direction of the transmitted wave. Other details describing well-known structures and systems often associated with ultrasound systems and associated devices have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1-6.

Figure 1:
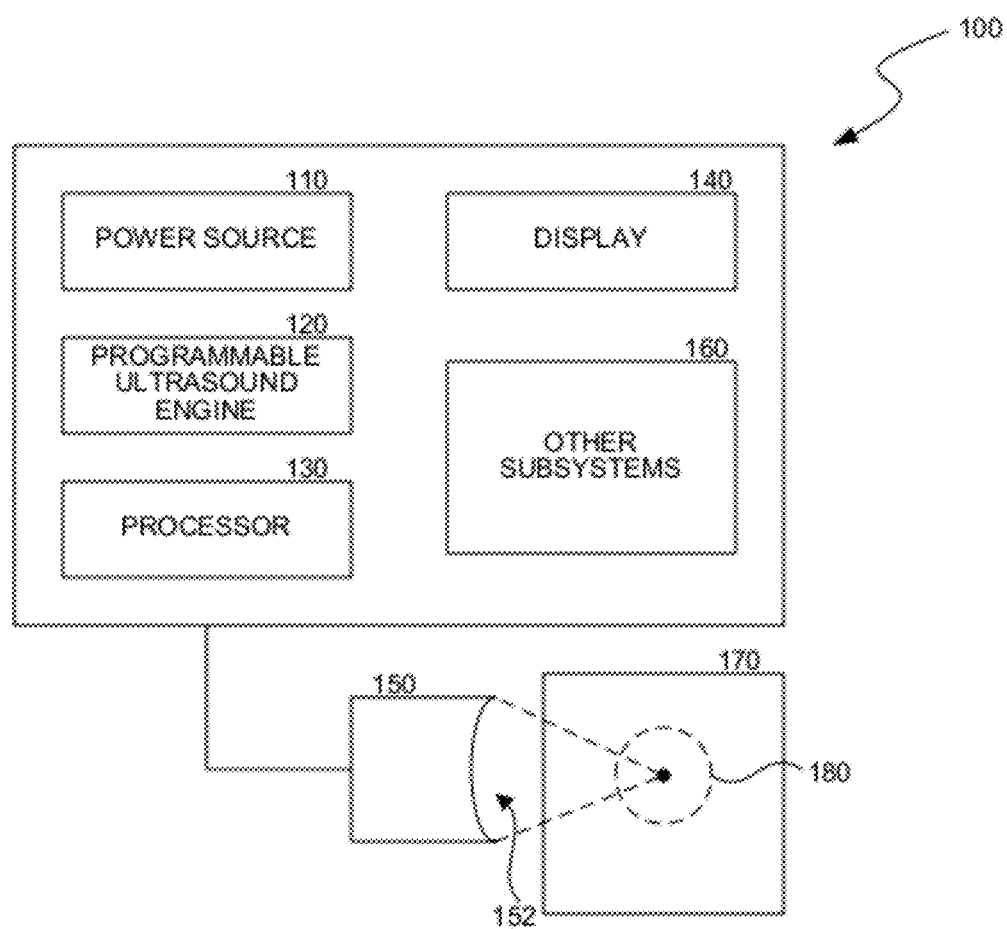
FIG. 1 is a schematic view of an ultrasound system configured in accordance with embodiments of the present technology.

FIG. 1 is a schematic view of an ultrasound system 100 configured in accordance with embodiments of the present technology. The ultrasound system 100 can include a power source 110, a programmable ultrasound engine 120, a processor 130, and a display 140 operably coupled to an ultrasound source 150. The ultrasound source 150 can be an ultrasound transducer device that has a generally similar configuration as any of the ultrasound transducer devices described in detail below with reference to FIGS. 2A-4. The programmable ultrasound engine 120, such as the Verasonics Ultrasound Engine manufactured by Verasonics Inc. of Redmond, Wash., can drive the ultrasound source 150 to transmit high amplitude acoustic waves that become nonlinear through propagation. For example, the excitation voltage can be increased to generate higher degrees of nonlinearity of the transmitted wave. In the context of imaging, wave penetration is proportional to the excitation voltage. Thus, stronger voltages (e.g., 50 V) increase imaging depths, while lower voltages can be used for shallower wave penetration. The processor 130 can be a computer or other suitable device that can receive and analyze data received by the ultrasound source 150 to generate images and other information on the display 140. The display 140 can be a monitor and/or other suitable visual imaging device. In other embodiments, the ultrasound system 100 can include additional devices and/or subsystems 160 that facilitate ultrasound scans and/or subsequent analysis. For example, the ultrasound system 100 can include filters, amplifiers, and/or other acoustic manipulation devices.

As shown in FIG. 1, the ultrasound source 150 can launch an acoustic wave toward a target site 180 in a medium (e.g., tissue) 170, and receive echoes as the acoustic wave reflects off of the tissue 170. The acoustic waves and resultant echoes can exit and enter the ultrasound source 150 through the same aperture 152. The ultrasound source 150 can have a wide receive bandwidth such that the echo data includes multiple harmonics of the transmit frequency. For example, in selected embodiments, the ultrasound source 150 can receive up to the fourth harmonic or higher (e.g., the eighth harmonic) depending upon the acoustic properties of the tissue or other transmit medium. The frequency rich echoes can be transmitted to the processor 130 and/or other subsystems 160 for image formation and further analysis. The resultant image displayed on the display 140 has an enhanced resolution due to the nonlinearity of the acoustic wave, and the relative changes in the amplitudes of the harmonic frequencies can be used to assess the response of the target tissue 170. As described in further detail below, the harmonic scatter can be used to dynamically estimate tissue properties (e.g., temperature).

Figure 2A:
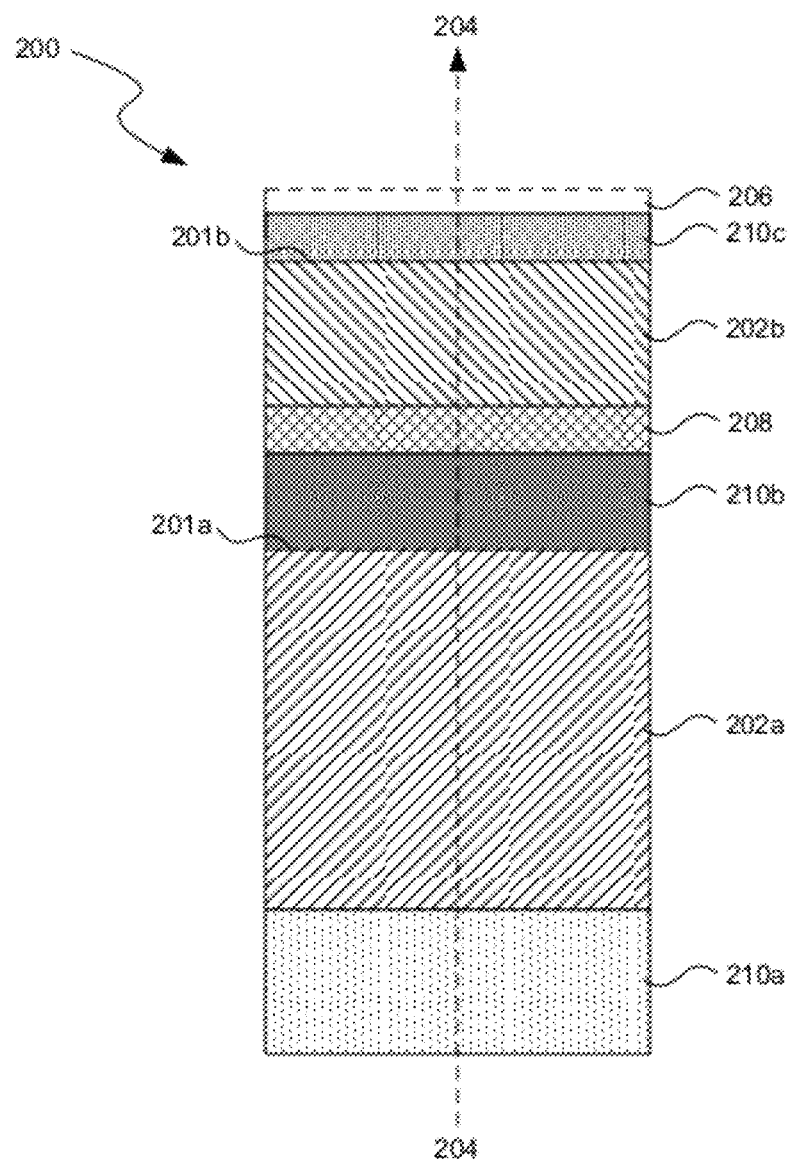
FIG. 2A is a schematic cross-sectional view of an ultrasound transducer device configured in accordance with an embodiment of the present technology.
Figure 2B:
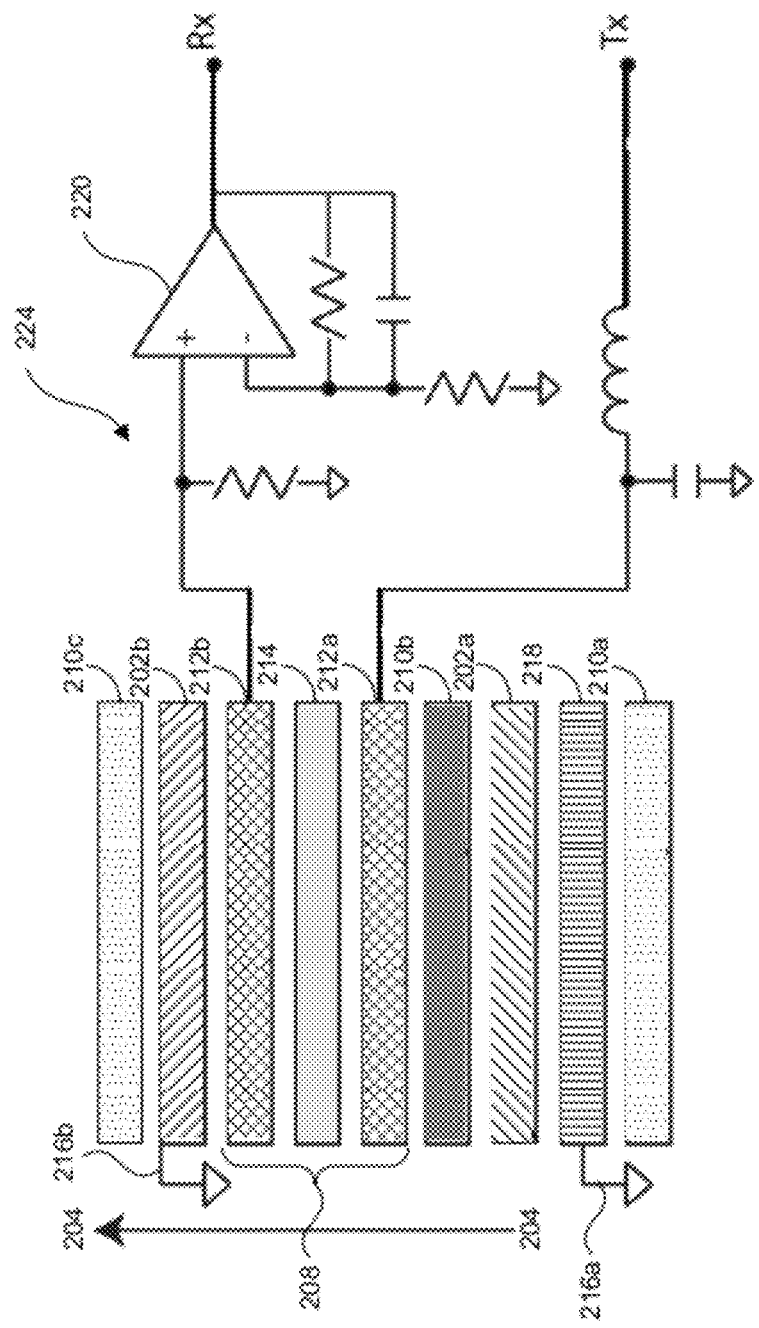
FIG. 2B is a schematic view of the ultrasound transducer device of FIG. 2A.

FIGS. 2A and 2B are schematic cross-sectional and schematic views, respectively, of an ultrasound transducer device 200 ("transducer device 200") configured in accordance with an embodiment of the present technology. Referring to FIG. 2A, the transducer device 200 can include a first transducer 202a that transmits high power acoustic waves and a second transducer 202b that has a wide bandwidth for receiving echoes from the acoustic waves. The first transducer 202a and the second transducer 202b can have corresponding first and second surfaces 201a and 201b that are oriented substantially parallel to one another and normal to an acoustic axis 204-204. This allows the acoustic waves to exit the transducer device 200 through an aperture 206 positioned over the first and second transducers 202a and 202b (as indicated by the arrow on the acoustic axis 204-204), and enter the transducer device 200 via the same aperture 206 (in the opposite direction of the arrow). As further shown in FIG. 2A, the transducer device 200 can also include an electrical connection layer 208 positioned between the first and second transducers 202a and 202b and impedance matching layers 210 (identified individually as a first impedance matching layer 210a, a second impedance matching layer 210b, and a third impedance matching layer 210c) positioned around and between the transducers 202a-b. During an ultrasound scan, the transducer device 200 can provide both a high conversion efficiency for transmitting high power acoustic waves and a wide bandwidth for receiving multiple harmonics of the transmit frequency.

The first transducer 202a can be composed of a first piezoelectric material that can be configured to transmit acoustic waves that become nonlinear through propagation and, optionally, receive echoes of the acoustic wave it transmits. The first piezoelectric material, for example, can be a piezoceramic, such as lead-zirconate-titanate (PZT) or a compound thereof, that has a high electro-acoustic conversion efficiency and also receives reflected acoustic waves. In other embodiments, however, the first piezoelectric material can be used solely to transmit acoustic waves. In further embodiments, the first transducer 202a can be made from other ceramic or non-ceramic piezoelectric compounds, single crystals (e.g., isotropic amorphous ceramics), and/or other suitable piezoelectric materials with high electro-acoustic conversion efficiencies for transmitting acoustic waves.

In various embodiments, the first transducer 202a can have a low range fundamental frequency (longer wavelength) to reduce the attenuation of nonlinear waves that occurs as the wave propagates through a medium. For example, a first transducer 202a having a fundamental frequency of approximately 2 MHz may be suitable for imaging depths in a body between approximately 4 cm and approximately 10 cm, such as abdominal and urological imaging. Higher fundamental frequencies (e.g., 5 MHz and higher) may be used at shallower imaging depths (i.e., smaller distance for wave attenuation) to obtain the desired harmonics. In other embodiments, microbubbles can be induced to enhance nonlinear scatter at shallower imaging depths.

The second transducer 202b can be composed of a second piezoelectric material that has a wide bandwidth for receiving echoes with rich frequency content from the reflected acoustic waves. In selected embodiments, for example, the second piezoelectric material can have a bandwidth of approximately 20 MHz, approximately 40 MHz, or higher. The wide bandwidth allows the second transducer 202b to receive the third harmonic of the transmit frequency or higher dependent upon the acoustic properties of the transmit medium. For example, the second transducer 202b may be able to detect up to the eighth harmonic in water or materials with acoustic properties similar to water, and up to the fourth harmonic in ex vivo tissue. In other embodiments, the bandwidth of the second piezoelectric material can be lower than 20 MHz, but still suitable for receiving multiple harmonics.

The second transducer 202b can be made from piezopolymer materials, such as polyvinylidene fluoride (PVDF) and/or a co-polymer of PVDF with Trifloroethylene (PVDF-TrFE). These materials exhibit a strong piezoelectric response and have an acoustic impedance that is closer to water than other piezoelectric materials (e.g., PZT), making them suitable sensors for ultrasound waves propagating in a medium with acoustic impedance similar to water (e.g., human soft tissue). In other embodiments, the second transducer 202b can include other copolymers and/or other suitable materials that have a wide bandwidth.

In the embodiment illustrated in FIG. 2A, the second transducer 202b is positioned over and substantially co-aligned with the first transducer 202a. The acoustic waves transmitted by the first transducer 202a, therefore, must propagate through the second transducer 202b before exiting the transducer device 200 via the aperture 206. Accordingly, the second transducer 202b can be made from a thin layer of the second piezoelectric material such that it has a substantially negligible effect (e.g., minimal attenuation) on the transmitted wave. In selected embodiments, for example, the second transducer 202b can have a thickness of approximately 110 µm or less. In other embodiments, the second transducer 202b may be thicker than 110 µm, but still have a substantially negligible effect on the transmitted wave.

The substantially co-aligned first and second transducers 202a and 202b can use the same aperture 206 to both transmit and receive acoustic waves. This single aperture 206 can be smaller in size than if the transducers 202a-b were spaced laterally apart, and thus reduce the likelihood that the transducer device 200 induces an undesired therapeutic effect in the transmit medium. The single aperture 206 can also simplify beam formation of echo data and enable detection of the echo data on both the first and second transducers 202a and 202b. In other embodiments, the first and second transducers 202a and 202b can be laterally offset, side-by-side, staggered, and/or otherwise oriented with respect to one another and include corresponding apertures such that the transmitted wave does not propagate through the second transducer 202b.

As shown in FIGS. 2A and 2B, the electrical connection layer 208 can be positioned between the first and second transducers 202a and 202b and electrically coupled to each such that it can route electrical connections to the transducers 202a-b. Referring to FIG. 2B, the electrical connection layers 208 can be patterned with first channels 212a and second channels 212b (e.g., traces) that are electrically isolated from one another by an insulating layer 214. The channels 212a-b can be made from copper, gold, and/or other electrically conductive material, and the insulating layer 214 can be made from a polymeric material and/or other suitable insulator. The first and second channels 212a and 212b can be separately connected to the corresponding transducers 202a-b such that the first channels 212a route transmit signals Tx to and from the first transducer 202a and the second channels 212b route receive signals Rx to and from the second transducer 202b. In various embodiments, such as when the first and second transducers 202a and 202b are substantially co-aligned, the first channels 212a can also route receive signals Rx to and from the first transducer 202a.

As shown in FIG. 2B, second channels 212b of the electrical connection layer 208 can be coupled to an impedance matching circuit 224 (e.g., on a printed circuit board ("PCB")) to isolate the second transducer 202b from the receive circuitry at a programmable imager (e.g., the processor 130 and the display 140 of FIG. 1). The second transducer 202b can also be coupled via the second channels 212b to a high impedance input of a non-inverting operational amplifier 220. The proximity of the second channels 212b to the second transducer 202b and the amplifier 220 (e.g., in a housing or handle of the transducer device 200) allows the amplifier 220 to improve the receive sensitivity of the second transducer 202a.

When the electrical connection layer 208 is positioned over the first transducer 202a, as shown in the illustrated embodiment, the electrical connection layer 208 can be configured to have a substantially negligible effect on the transmission of the acoustic wave as it propagates from the first transducer 202a. The electrical connection layer 208, for example, can be a thin flex circuit (e.g., a flex circuit manufactured by Microconnex, Inc. of Snoqualmie, Wash.) that includes traces (e.g., copper, gold, etc.) isolated from one another by a polymer material and/or other flexible and insulative material. In one embodiment, the traces can have a thickness of approximately 2 μm and the polymer material can have a thickness of approximately 25 μm, such that the combined thickness of less than 30 μm is nearly acoustically transparent to frequencies in lower megahertz ranges (e.g., frequencies less than approximately 2 MHz). In other embodiments, the electrical connection layer 208 can have smaller or greater thicknesses (e.g., approximately 48 μm) that are substantially acoustically transparent to the fundamental frequency of the first transducer 202a. In further embodiments, the electrical connection layer 208 can be made from different materials and/or other suitable structures. For example, the traces can be patterned on a metalized layer on the second transducer 202b. In still further embodiments, the electrical connection layer 208 can be positioned elsewhere on the transducer device 200 such that it does not affect the transmission of acoustic waves from the first transducer 202a.

The impedance matching layers 210 can be used to passively improve electro-acoustic conversion efficiency of the transducers 202a-b and/or to maximize radiation in the forward direction. In the embodiment illustrated in FIGS. 2A and 2B, for example, a backing layer or first impedance matching layer 210a can be positioned behind the first transducer 202a to provide support for the first and second transducers 202a and 202b and enhance radiation in the forward direction (i.e., in the direction of the arrow on the acoustic axis 204-204). The second impedance matching layer 210b can be positioned forward of the first transducer 202a to enhance radiation efficiency of the first transducer 202a during wave transmission, and the third impedance matching layer 210c can be positioned over the second transducer 202b to enhance the conversion of acoustical energy to electrical energy during reception. The impedance matching layers 210 can have varying acoustic impedances. For example, the first impedance matching layer 210a can have an acoustic impedance of approximately 3 MRayl, and the second impedance matching layer 210b can have an acoustic impedance of approximately 6 MRayl. In other embodiments, however, the acoustic impedances can be higher or lower. In further embodiments, some or all of the impedance matching layers 210 can be omitted and/or additional impedance matching layers 210 can be included in the transducer device 200. Additionally, the composition of the electrical connection layer 208 and/or the second transducer 202b can be chosen to further improve radiation efficiency and enhance the transmission from the first transducer 202a.

Referring still to FIG. 2B, the transducer device 200 can further include a first ground 216a coupled to a metalized layer 218 behind the first transducer 202a and a second ground 216b on the forward-most surface of the second transducer 202b. The first ground 216a can at least substantially prevent the flow of electricity backward toward other circuitry in the transducer device 200, the user (e.g., into a handle of the transducer device 200), and/or other system components (e.g., the programmable ultrasound engine 120, the processor 130, and the display 140 of FIG. 1). The second ground 216b can at least substantially prevent the flow of electricity forward into the transmit medium (e.g., tissue). In other embodiments, the transducer device 200 can include additional grounds corresponding to additional transducers.

As discussed above, in the embodiment illustrated in FIGS. 2A and 2B, the acoustic waves transmitted by the first transducer 202a must travel through the electrical connection layer 208, the second transducer 202b, and selected impedance matching layers 210 before exiting the transducer device 200 via the aperture 206. Accordingly, the elements in front of the second impedance matching layer 210b (i.e., those elements that may negatively interfere with the transmission of the acoustic wave from the first transducer 202a) can be configured to have a combined thickness that is a fraction of the acoustic wavelength of the transmitted wave, and thereby have a substantially negligible effect on the transmitted wave. For example, the second transducer 202b and the electrical connection layer 208 can have a combined thickness of less than approximately 100 μm, which a is small fraction of the 1.5 mm wavelength generated by a 1 MHz wave in water. In other embodiments, the thickness of the layers forward of the first transducer 202a can be larger or smaller.

The layers of elements of the transducer device 200 (e.g., the transducers 202a-b, the electrical connection layer 208, the impedance matching layers 210, etc.) can be joined together using a low viscosity and electrically nonconductive epoxy and/or other suitable adhesive. The electrical connections between the transducers 202a-b and the electrical connection layer 208 (e.g., the first and second channels 212a and 212b) can be maintained by placing the layers of elements under static pressure while the epoxy cures. In other embodiments, the electrical connections can otherwise be maintained during formation of the transducer device 200 and/or the layers of the transducer device 200 can be joined using other suitable fastening methods known to those skilled in the art.

The transducer device 200 can be configured such that the first transducer 202a can transmit nonlinear acoustic waves at a transmit frequency and the second transducer 202b can receive multiple harmonics of the transmit frequency with broadband sensitivity. The use of nonlinear ultrasound propagation can enhance the resolution of ultrasound imaging due to the higher signal and contrast to noise of the harmonic frequencies than the transmit frequency. Additionally, the detection and processing of harmonic scatter by the second transducer 202b and, optionally, the first transducer 202a can be used to characterize the static and dynamic properties of the transmit medium (e.g., tissue). Temperature changes, for example, significantly affect the nonlinear propagation of the acoustic wave, and the resultant attenuation of the detected harmonics in the received echo can be used to derive temperature sensitive properties and/or the temperature of the tissue. Accordingly, in various embodiments, the transducer device 200 can be used to monitor therapeutic heating technologies, such as high intensity focused ultrasound ("HIFU"), ultrasound-induced hyperthermia, and/or other ultrasound and non-ultrasound based treatments. For example, the transducer device 200 can be used to monitor temperature and/or temperature sensitive properties during and after a therapeutic treatment performed by a separate device (e.g., a separate transducer). In the case of ultrasound-based therapies, the transducer device 200 can be combined with the therapeutic transducer (e.g., positioned over or proximate to the therapeutic transducer), or the first transducer 202a can serve the therapy source.

Figure 3:
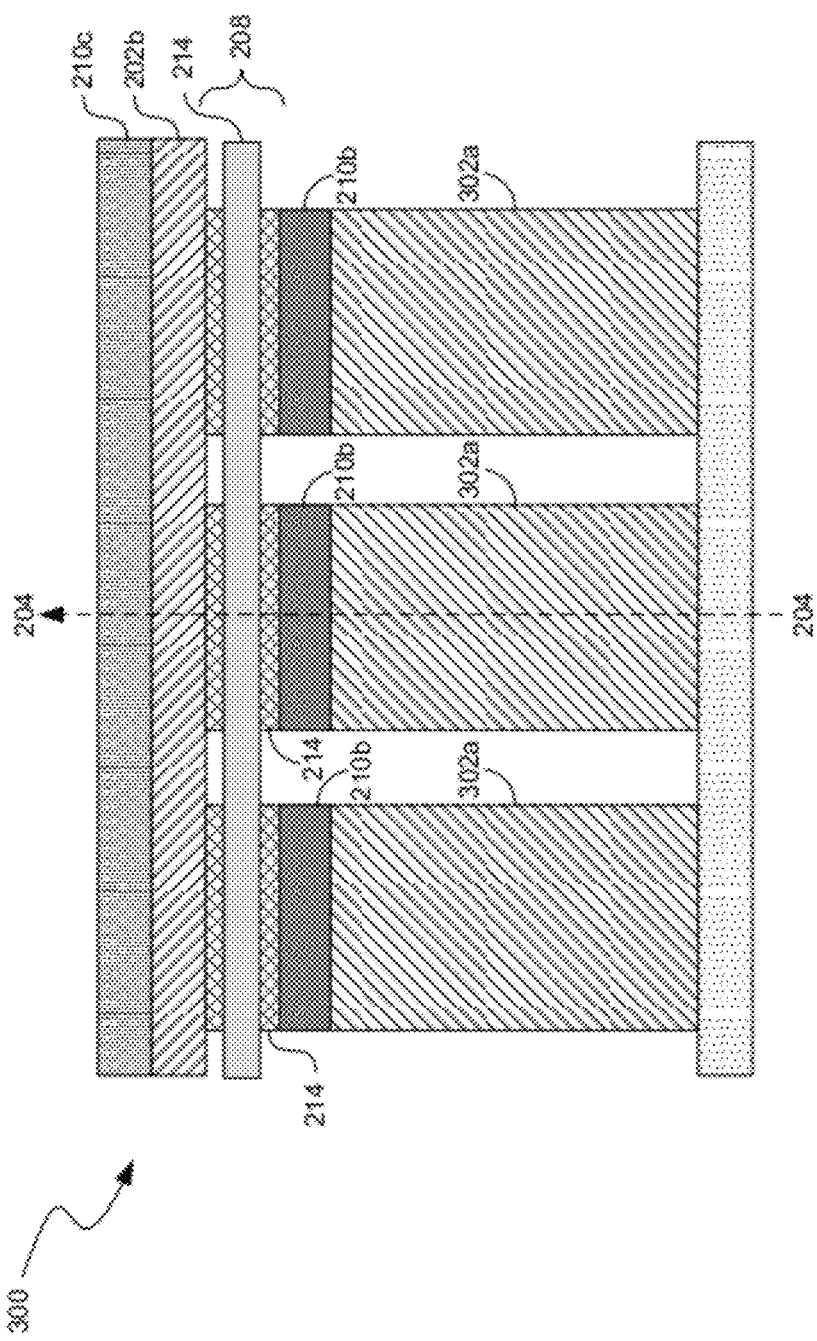
FIG. 3 is a schematic cross-sectional view of an ultrasound transducer device configured in accordance with another embodiment of the present technology.

FIG. 3 is a schematic cross-sectional view of an ultrasound transducer device 300 ("transducer device 300") configured in accordance with another embodiment of the present technology. The transducer device 300 includes a number of features generally similar to the transducer device 200 described above with reference to FIGS. 2A and 2B. For example, the transducer device 300 includes the second transducer 202b, the electrical connection layer 208, and impedance matching layers 210 substantially co-aligned with one another along the acoustic axis 204-204. Rather than a single first transducer 202a (FIGS. 2A and 2B), however, the transducer device 300 includes an array of first transducers 302a that can operate independently of one another. For illustrative purposes, FIG. 3 shows an array of three first transducers 302b, but it will be understood by those skilled in the art that the transducer device 300 can include a much larger array of the first transducers 302a. In selected embodiments, for example, the transducer device 300 can include an array of 32, 128, 256, or more transducer elements.

As shown in FIG. 3, each of the first transducers 302a can be independently coupled to separate first channels 212a in the electrical connection layer 308. The first impedance layer 210a can span across the backside of the array of first transducers 302a. Similarly, the second transducer 202b and the third impedance matching layer 210c both can extend over the front side of the first transducer array in unsingulated layers. The second impedance matching layer 210b, however, can be separated into discrete portions over the individual first transducers 302a to facilitate separate electrical connections between the first transducers 302a to the corresponding first channels 212a. In other embodiments, the impedance matching layers 210 and/or the second transducer 202b can be diced or otherwise separated into individual elements over each of the first transducers 302a such that the array comprises a plurality of independent transducer elements (e.g., a plurality of the transducer devices 200 shown in FIG. 2A). In further embodiments, the first and second transducers 302a and 202b can be staggered, offset, and/or otherwise positioned with respect to one another in an array.

Similar to the transducer device 200 described above with reference to FIGS. 2A and 2B, the transducer device 300 can generate nonlinear waveforms that enhance the resolution of ultrasound imaging, and can detect echo data that is rich in frequency content to assess static and dynamic properties of a transmit medium. The independent coupling of the first transducers 302a with the first channels 212a enables electronic phasing of the first transducer 302a that can steer acoustic waves and thereby further enhance imaging resolution. Additionally, the array of transducers 302 and the corresponding aperture that accommodates the array of transducers 302 increases the penetration depth of the transducer device 300 as compared to a single element transducer.

Figure 4:
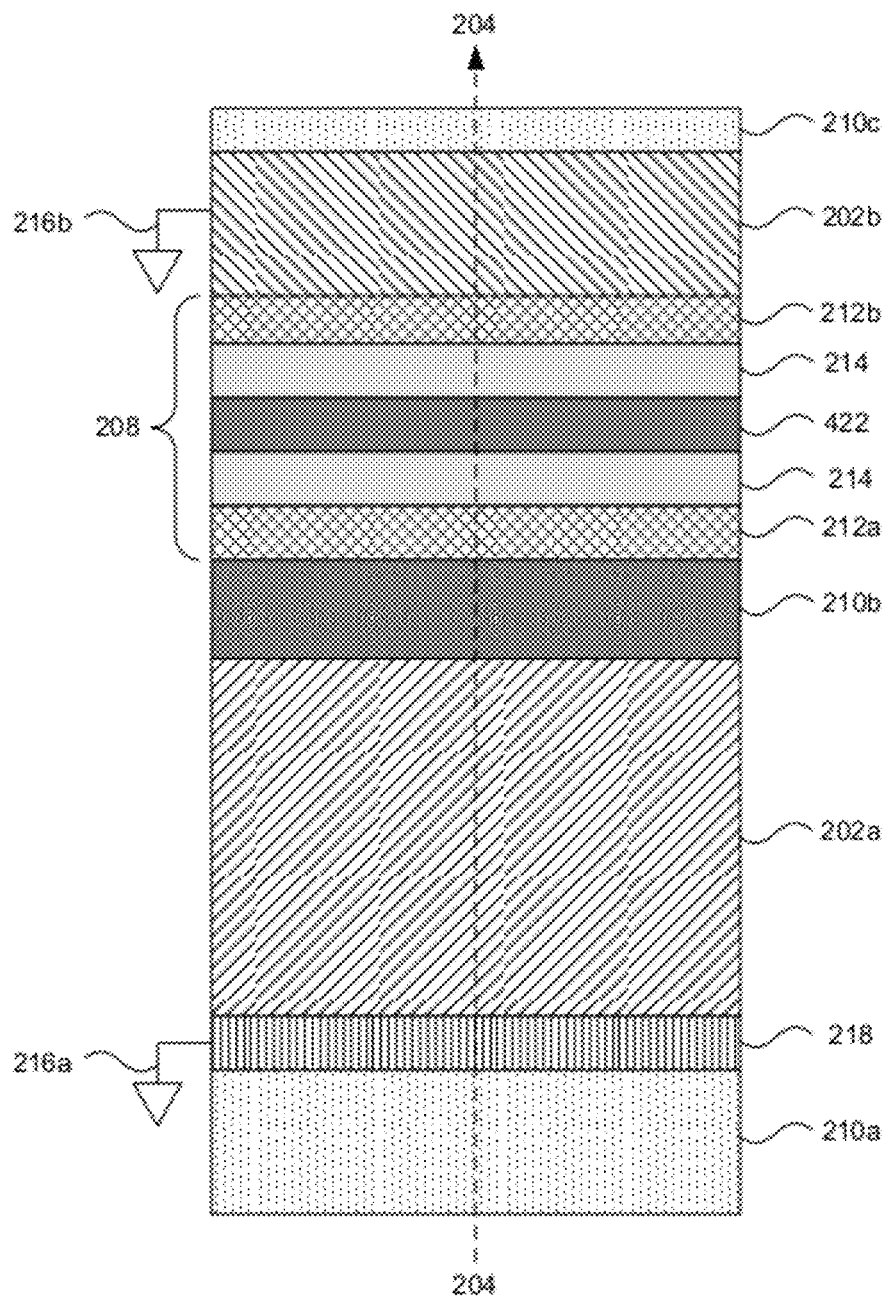
FIG. 4 is a schematic cross-sectional view of an ultrasound transducer device configured in accordance with a further embodiment of the present technology.

FIG. 4 is a schematic cross-sectional view of an ultrasound transducer device 400 ("transducer device 400") configured in accordance with a further embodiment of the present technology. The transducer device 400 includes a number of features generally similar to the features of the transducer device 200 shown in FIGS. 2A and 2B. As shown in FIG. 4, the transducer device 400 further includes a damping layer 422 between the first and second transducers 202a-b to inhibit reverberations and attenuate bounce back of the transmitted wave between the first and second transducers 202a and 202b. The damping layer 422 can be thin such that it, in combination with the other layers forward of the first transducer 202a, has a negligible effect on the transmission of the acoustic wave. For example, in selected embodiments, the damping layer 422 can have a thickness between approximately 1 mm and approximately 3 mm. In other embodiments, however, the damping layer 422 can be thicker or thinner and/or the transducer device 400 can include additional damping layers positioned between or around the transducers 202a-b. The damping layer 422 can be made from an elastomeric material, such as rubber, silicone polymers, loaded silicone polymers, and/or other suitable materials, and can be joined with the other layers of the transducer device 400 using an adhesive or other suitable fastening mechanism.

Figure 5A:
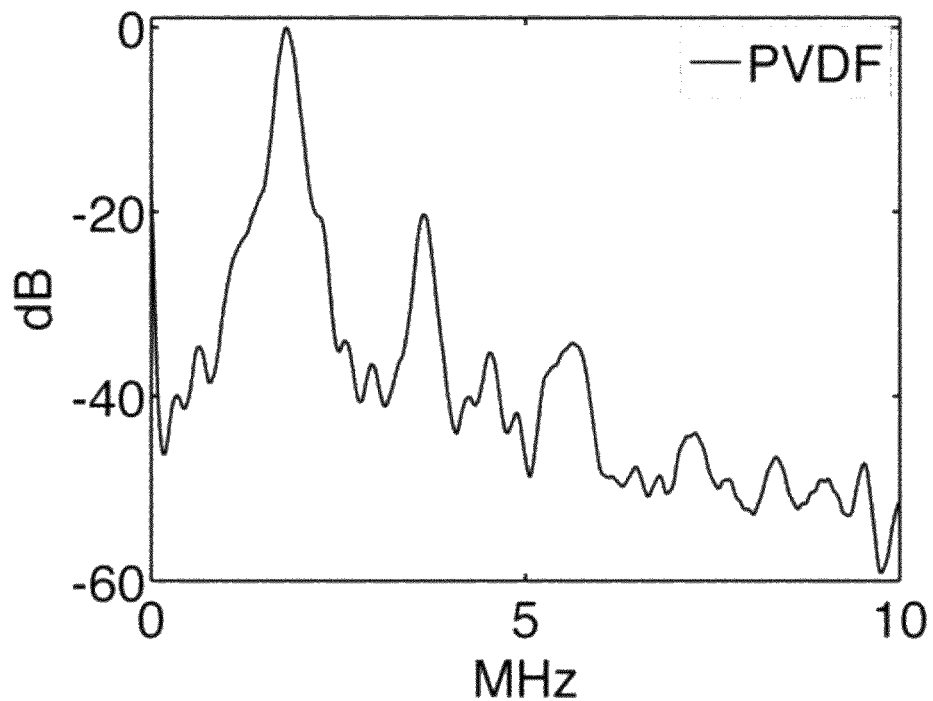
FIGS. 5A and 5B are graphs illustrating pulse echo feedback received by ultrasound transducer devices configured in accordance with embodiments of the present technology.
Figure 5B:
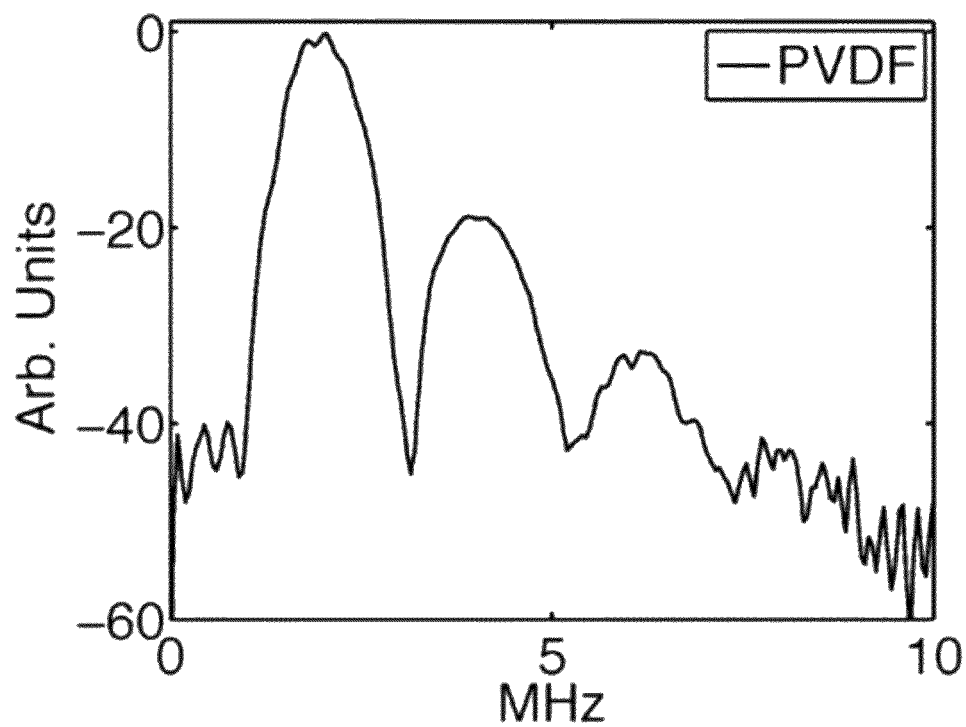

Additionally, the damping layer 422 can smooth or flatten the frequency response of the second transducer 202b. FIGS. 5A and 5B, for example, are graphs illustrating pulse echo feedback received by ultrasound transducer devices excluding and including a damping layer, respectively. Without a damping layer (FIG. 5A), the transducer device receives up to approximately the fourth harmonic of the fundamental, with the second harmonic at approximately −20 dB, the third harmonic at approximately −34 dB, and the fourth harmonic at approximately −44 dB. As shown in FIG. 5B, the addition of the damping layer can reduce the notching in the harmonic scatter and generally smooth the echo feedback such that higher harmonics (e.g., the fourth harmonic) are easier to distinguish. In other embodiments, the damping layers can substantially smooth echo feedback that includes harmonics beyond the fourth harmonic.

Figure 6:
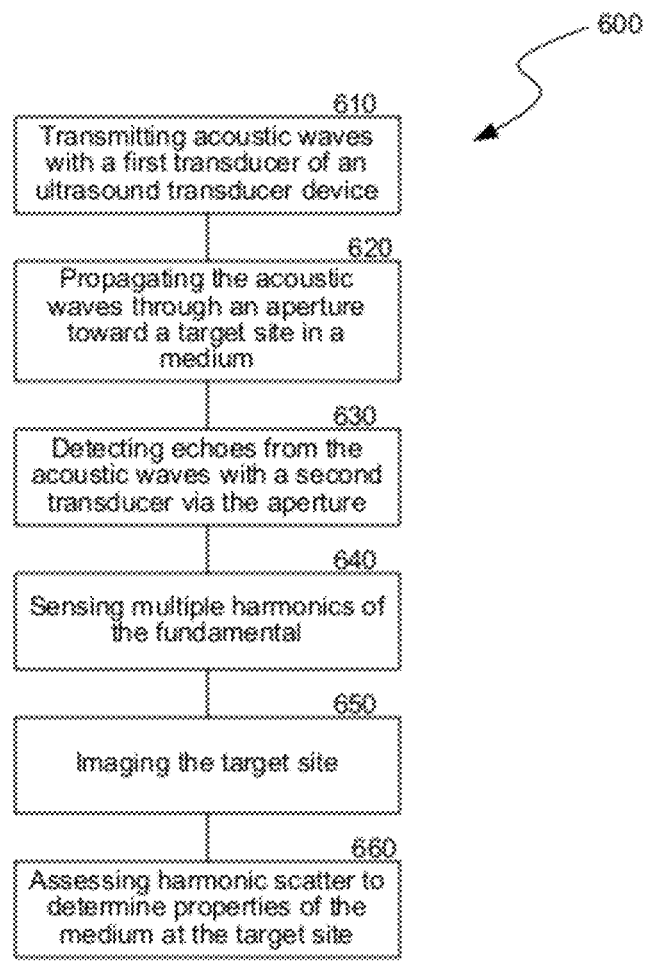
FIG. 6 is a block diagram illustrating a method of performing an ultrasound scan in accordance with an embodiment of the present technology.

FIG. 6 is a block diagram illustrating a method 600 of performing an ultrasound scan in accordance with an embodiment of the present technology. The method 600 can include transmitting acoustic waves with a first transducer of an ultrasound transducer device (block 610), and propagating the acoustic wave through an aperture toward a target site in a medium (block 620). Like the first transducers 202a discussed above, the first transducer can include a piezoceramic material (e.g., PZT) and/or other piezoelectric materials that can transmit acoustic waves that become non-linear through propagation. The nonlinearity of the acoustic wave can enhance resolution of the subsequently imaged target site. In other embodiments, the first transducer can be one of an array of first transducers that can further enhance imaging and/or increase the imaging depth.

The acoustic wave can reflect off of the target site in the medium, and the method 600 can continue by detecting echoes from the acoustic waves with a second transducer via the aperture (block 630). As described above, the second transducer can be made from a piezoelectric material that is different from the piezoelectric material of the first transducer in that it has a wider broadband reception. For example, in selected embodiments, the second transducer can have a frequency of approximately 20 MHz to approximately 40 MHz, whereas the first transducer can have a low frequency of less than 5 MHz. In other embodiments, the frequencies of the first and second transducers can be higher or lower. The wide broadband reception allows the second transducer to receive echoes with rich frequency content. This allows the second transducer to sense multiple harmonics of the fundamental frequency (block 640). For example, the second transducer can sense up to the third harmonic or beyond depending upon the acoustic properties of the medium.

In various embodiments, the first and second transducers can be substantially co-aligned with the acoustic axis such that the same aperture can be used to both transmit the acoustic waves and receive the echoes thereof. The ultrasound transducer device can thus be more compact than one that necessitates separate openings for the transmit and receive functions. Additionally, the alignment of the first and second transducers allows the first transducer to participate in the reception of echo feedback from the wave it transmits.

The method 600 can further include imaging the target site (650) and/or assessing the harmonic scatter to determine properties of the medium at the target site (660). As discussed above, the method 600 can generate high resolution images and detect multiple harmonics of the transmit frequency that can be used for tissue characterization and/or temperature monitoring of the target site. Accordingly, in various embodiments, the method 600 can be used to image the target site and/or monitor temperature and/or temperature sensitive properties during and after non-ultrasound and ultrasound based therapies, such as HIFU, ultrasound induced hyperthermia, and/or other ultrasound therapies. For example, the images can be used to identify and differentiate mechanical effects from thermal effects during HIFU therapy. In the case of ultrasound induced hyperthermia, for example, tissue heating can take minutes such that the ultrasound transducer device can obtain frequent interrogation of the tissue for imaging and monitoring during heating.

The ultrasound transducer device can be used in conjunction with a separate therapy device (e.g., a therapy transducer) and/or as the therapy source itself. For example, the first transducer can transmit acoustic waves that induce hyperthermia and/or HIFU tissue ablation, while the second transducer can be positioned over the first transducer to receive the frequency rich echoes. In other embodiments, the first and second transducers can be arranged in an array over, with, or proximate to the therapy source to provide imaging and monitoring of the target site during therapy. In further embodiments, the ultrasound transducer device can be completely separate from the therapy source but aligned with the target site to perform monitoring and imaging.

From the foregoing, it will be appreciated that specific embodiments of the technology have been described herein for purposes of illustration, but that various modifications may be made without deviating from the disclosure. In some examples, the ultrasound transducer devices of FIGS. 2A-4 can include additional impedance matching layers 210. For example, the transducer devices can include several second impedance matching layers 210b over the first transducer 202a to enhance transmission of high amplitude acoustic waves and/or several third impedance matching layers 210c over the second transducer 202b to increase the bandwidth of the second transducer 202b and thereby enhance the reception of harmonics. Additionally, an acoustic lens can be added to any of the ultrasound transducer devices described above to enhance the focus of the transmitted wave. Certain aspects of the new technology described in the context of particular embodiments may be combined or eliminated in other embodiments. For example, the damping layer 422 of FIG. 4 can be combined with the array of transducers 302 shown in FIG. 3. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. An ultrasound device, comprising:
a first array of first transducers, the first transducers oriented along an acoustic axis and comprising a first piezoelectric material configured to transmit nonlinear acoustic waves;
a second array of second transducers oriented along the acoustic axis and substantially parallel to the first transducers, the second transducers comprising a second piezoelectric material configured to receive echoes from the acoustic waves, wherein the acoustic waves have a fundamental frequency, and wherein the second transducers are configured to sense up to at least a third harmonic of the fundamental frequency; and
an electrical connection layer between the first and second arrays and electrically coupled to the first and second transducers, wherein the electrical connection layer comprises first channels electrically coupled to the first transducers and second channels electrically coupled to the second transducers and electrically isolated from the first transducers.

2. The ultrasound device of claim 1 wherein:
the first transducers are substantially co-aligned with corresponding second transducers;
the first piezoelectric material comprises lead zirconate titanate;
the second piezoelectric material comprises polyvinylidene fluoride having a thickness of less than approximately 110 µm; and
the ultrasound device further comprises:
an aperture over the first and second transducers, the second transducers being proximate to the aperture, wherein the acoustic waves are configured to exit the ultrasound device via the aperture and the echoes from the acoustic waves are configured to enter the ultrasound device via the aperture;

a backing layer on a back surface of the first transducers, the backing layer being configured to enhance radiation forward of the first transducers;

a first impedance matching layer over the first transducers; and a second impedance matching layer over the second transducers.

3. The ultrasound device of claim 1, further comprising an aperture over the first and second transducers, wherein the acoustic waves are configured to exit the ultrasound device via the aperture and the echoes from the acoustic waves are configured to enter the ultrasound device via the aperture.

4. The ultrasound device of claim 1 wherein:

the first piezoelectric material comprises lead zirconate titanate; and the second piezoelectric material comprises polyvinylidene fluoride.

5. The ultrasound device of claim 1 wherein:

the first piezoelectric material is configured to transmit higher power acoustic waves than the second piezoelectric material; and the second piezoelectric material is configured to receive a wider bandwidth of echoes than the first piezoelectric material.

6. The ultrasound device of claim 1 wherein the ultrasound device is configured to transmit high intensity ultrasound waves.

7. The ultrasound device of claim 1 wherein:

the ultrasound device has a fundamental frequency having a wavelength; and the second transducers and the electrical connection layer have a combined thickness that is a fraction of the wavelength of the fundamental frequency.

8. The ultrasound device of claim 1, further comprising a damping layer between the first and second transducers, wherein the damping layer is configured to decrease reverberations of the acoustic waves between the first and second transducers and smooth frequency response of the second transducers.

9. The ultrasound device of claim 1 wherein the electrical connection layer comprises a flex circuit having a thickness such that the electrical connection layer is substantially acoustically transparent to a frequency of less than approximately 5 MHz.

10. The ultrasound device of claim 1, further comprising an amplifier operably coupled to and positioned proximate to the second transducer.

11. An ultrasound device, comprising:

a first transducer having a first side opposite a second side, the first transducer comprising a piezoceramic material;

a second transducer having a first side opposite a second side, the second transducer comprising a piezopolymer material, wherein the first and second transducers are stacked such that the second sides face one another;

a flex circuit between the first and second transducers and operably coupled to the first and second transducers, wherein the flex circuit comprises first channels electrically coupled to the first transducer and second channels electrically coupled to the second transducer and electrically isolated from the first transducers; and an aperture proximate to the first side of the second transducer, wherein the first transducer is configured to transmit acoustic waves through the aperture that become nonlinear through propagation and the second transducer is configured to receive echoes from the acoustic waves through the aperture, and wherein the second transducer detects up to at least a third harmonic in the echo.

12. The ultrasound device of claim 11, further comprising:

a backing layer at the first side of the first transducer; and an impedance matching layer over the second side of the first transducer.

13. The ultrasound device of claim 11 wherein the second transducer has a thickness of less than approximately 110 µm.

14. The ultrasound device of claim 11 wherein the second transducer has bandwidth of at least approximately 20 MHz.

15. The ultrasound device of claim 11 wherein the flex circuit has a thickness of less than approximately 50 µm.

16. The ultrasound device of claim 11 wherein:

the first transducer is one of a plurality of first transducers arranged in a first array; and the second transducer is one of a plurality of second transducers arranged in a second array over the first array.

17. The ultrasound device of claim 11, further comprising an elastomeric layer between the first and second transducers.

18. A method of performing an ultrasound scan, the method comprising:

transmitting acoustic waves with a first array of first transducers, the first transducers comprising a piezoceramic material;

propagating the acoustic waves through an aperture toward a medium, wherein the acoustic waves become nonlinear through propagation;

detecting echoes from the acoustic waves with a second array of second transducers via the aperture, the second transducers comprising a piezopolymer material, wherein the first and second transducers are oriented substantially parallel to one another along an acoustic axis with an electrical connection layer between the first and second transducers, wherein the electrical connection layer comprises first channels electrically coupled to the first transducers and second channels electrically coupled to the second transducers and electrically isolated from the first transducers; and sensing up to at least a third harmonic in the detected echoes with the second transducers.

19. The method of claim 18, further comprising:

damping reverberations of the acoustic waves between the first and second transducers with an elastomeric material; and smoothing a frequency response of the second transducers with the elastomeric material.

20. The method of claim 18 wherein:

transmitting acoustic waves comprises propagating the acoustic waves toward a tissue, the acoustic waves having a fundamental frequency; and the method further comprises measuring attenuation in the sensed harmonics to determine a temperature in the tissue.

21. The method of claim 18 wherein:

transmitting acoustic waves comprises transmitting therapeutic ultrasound waves toward a tissue; and the method further comprises monitoring at least one of temperature and temperature sensitive characteristics in the tissue during transmission of therapeutic waves by detecting harmonic scattering beyond a second harmonic of a fundamental frequency.

22. An ultrasound device, comprising:

a first array of first transducers, wherein the individual first transducers are oriented along an acoustic axis, and wherein the first transducers are configured to transmit ultrasound waves that become nonlinear through propagation;

a second array of second transducers substantially aligned with the first transducers along the acoustic axis, wherein the second transducers are configured to detect echo data including up to at least the third harmonic of the nonlinear ultrasound waves transmitted by the first transducers, and wherein the first transducers comprise a different transducer material than the second transducers; and an electrical connection layer between the first and second arrays, wherein the electrical connection layer comprises first channels electrically coupled to the first transducers and second channels electrically coupled to the second transducers and electrically isolated from the first transducers.

* * * * *

UNITED STATES PATENT AND TRADEMARK OFFICE
CERTIFICATE OF CORRECTION

PATENT NO. : 8,500,643 B2
APPLICATION NO. : 13/158299
DATED : August 6, 2013
INVENTOR(S) : Curra et al.

It is certified that error appears in the above-identified patent and that said Letters Patent is hereby corrected as shown below:

In the Specification

Column 1, line 20, delete "disclosure" and insert -- invention --, therefor.

Column 1, line 21, delete "R01DK075090" and insert -- grant R01 DK075090, --, therefor.

Column 1, line 22, delete "(NIH)", therefor.

Signed and Sealed this
Second Day of September, 2014

Michelle K. Lee
*Deputy Director of the United States Patent and Trademark Office*